United States Patent [19]

Greco

[11] Patent Number: 4,489,004

[45] Date of Patent: Dec. 18, 1984

[54] PROCESS FOR FORMING VANADIUM PHOSPHORODITHIOATE COMPOUNDS

[75] Inventor: Carl C. Greco, Garnerville, N.Y.

[73] Assignee: Stauffer Chemical Company, Westport, Conn.

[21] Appl. No.: 439,708

[22] Filed: Nov. 8, 1982

[51] Int. Cl.³ ................................................ C07F 9/00
[52] U.S. Cl. ................................................ 260/429 R
[58] Field of Search ..................................... 260/429 R

[56] References Cited

U.S. PATENT DOCUMENTS

| | | | |
|---|---|---|---|
| 3,168,497 | 2/1965 | Twitchett | 260/429.9 X |
| 3,290,342 | 12/1966 | Stern et al. | 260/429 R |
| 3,428,662 | 2/1969 | Millendorf et al. | 260/429 R X |
| 3,595,844 | 7/1971 | Huerta et al. | 260/429 R |
| 3,595,890 | 7/1971 | Huerta et al. | 260/429 R |
| 3,896,094 | 7/1975 | Visser | 526/121 |

OTHER PUBLICATIONS

Furiani et al., J. Chem. Soc. (A), pp. 2929–2934 (1970).
Cavell et al., Inorg. Chem. VII (7), pp. 1591–1597 (1972).

Primary Examiner—Helen M. S. Sneed
Attorney, Agent, or Firm—Richard P. Fennelly

[57] ABSTRACT

Vanadium dialkyl phosphorodithioate compounds are formed by the reaction of dialkyl phosphorodithioate acid with a vanadium halide in the presence of a substance capable of removing by-product hydrogen halide from the reaction medium.

15 Claims, No Drawings

PROCESS FOR FORMING VANADIUM PHOSPHORODITHIOATE COMPOUNDS

BACKGROUND OF THE INVENTION

1. Field of the Invention

The present invention relates to a process for the formation of vanadium phosphorodithioate compounds.

2. Description of the Prior Art

Vanadium dialkyl phosphorodithioate compounds have been described as effective catalysts in the preparation of copolymers of alpha olefins, e.g., ethylene/propylene rubber and ethylene/propylene/diene terpolymers. In U.S. Pat. No. 3,896,094 to H. D. Visser et al. such compounds are said to be manufactured by reaction between a vanadium halide or sulfate and a sodium or ammonium salt of a dialkylphosphorodithioic acid.

Reaction between the dialkylphosphorodithioic acid and vanadium halide to form vanadium dialkyl phosphorodithioate compounds in the absence of any substance to remove hydrogen halide by-product from the reaction medium is shown in C. Furlani et al., J. Chem. Soc. (A), 1970, 2929–2934. For example, on page 2929 of that reference vanadium (III) tris-O,O-di-n-propyl phosphorodithioate was indicated to have been prepared by reaction of vanadium trichloride with the corresponding acid. The resulting vanadium compound (or complex) was said to be stable for long periods under nitrogen but rapidly decomposed in air giving a black precipitate. Attempts to separate such a compound by extraction with organic solvents and then evaporation were unsuccessful.

SUMMARY OF THE PRESENT INVENTION

The present invention is a process for the formation of vanadium dialkyl phosphorodithioate compounds by reaction of dialkyl phosphorodithioic acid with a vanadium halide in the presence of a substance capable of removing by-product hydrogen halide from the reaction medium.

DESCRIPTION OF THE PREFERRED EMBODIMENTS

The present process relates to the formation of vanadium phosphorodithioates having the formula:

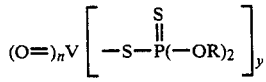

where R is a $C_1$–$C_{10}$ alkyl group, n is either 0 (when y is either 2, 3 or 4) or 1 (when y is 2 or 3).

Compounds of the above formula are formed from the corresponding phosphorodithioic acid having the formula

by reaction with a suitable vanadium halide of the formula

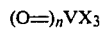

with X being a halogen atom, preferably chlorine. The vanadium halide is the source of the multivalent vanadium atom. When $VCl_3$ is used, for example, vanadium (III) compounds result; when $VOCl_3$ is employed, vanadium (V) compounds are formed; when $VCl_4$ or $VOCl_2$ are used, vanadium (IV) compounds are formed.

The reaction of the present invention is conducted in the presence of an effective amount of a substance capable of removing hydrogen halide by-product, e.g., HCl, from the reaction medium. For example, the sparging of the reaction medium with a suitable inert gas, e.g., nitrogen, can be used to accomplish removal of this by-product. Heating of the reaction mixture can also be employed to assist in the removal of hydrogen halide by-product. Chemical acid acceptors, e.g., amine acid acceptors, can also be employed especially when vanadium halide reagents of relatively low reactivity and/or relative insolubility in the reaction medium are employed.

The acid and vanadium chloride are preferably reacted with one another using approximate stoichiometric amounts since it is very difficult to remove any excess acid from the reaction medium after the reaction has been completed. For example, use of $VCl_3$ or $VOCl_3$ require use of 3:1 moles acid to vanadium compound; $VOCl_2$, use of 2:1 moles acid to vanadium; and $VCl_4$, use of 4:1 moles acid to vanadium. The reaction can be conducted in an inert organic solvent medium, if desired (e.g., toluene). The reaction proceeds at ambient temperature although temperatures of from about 50° C. to about 90° C. can be used, if desired.

The present invention is illustrated by the Examples which follow.

EXAMPLE 1

Into a one liter flask equipped with a gas inlet, stirrer, condenser and dropping funnel was added 110 gm. (0.513 mole) of di-n-propyl phosphorodithioic acid. The acid was diluted with 350 cc. of toluene. In the dropping funnel was placed 30 gm. (0.173 mole) of $VOCl_3$. The $VOCl_3$ was added to the acid in the reaction flask over a period of 60 minutes while a stream of nitrogen was passed through the solution to remove by-product HCl. After the addition had been completed, the reaction mixture was heated to 65°–70° C. to remove substantially all traces of HCl. The mixture was then cooled and stripped of solvent at reduced pressure (about 10 mm. of Hg). The solid which remained was washed twice with 50 cc. aliquots of heptane and was then vacuum dried. The yield was slightly over 140 grams. Analysis of the product showed the following elements: Sulfur—20.1 wt. %; Phosphorus—11.3 wt. %; and Vanadium—5.2 wt. %. The crude product was found to contain 20% toluene which was residual toluene which had not distilled off. The yield of desired product was almost quantitative and was around 80% pure.

EXAMPLE 2

The same procedure used in Example 1 was employed with the exception that $VCl_3$ was used in place of $VOCl_3$. The yield of desired product was judged to be less than 10% as determined by the amount of HCl evolution coming from the reaction medium. $VCl_3$ has a lower reactivity than the $VOCl_3$ reagent used in Example 1. In addition, $VCl_3$ is insoluble in the reaction media used, whereas $VOCl_3$ is soluble.

EXAMPLE 3

Into a 250 ml. flask equipped with a gas inlet, stirrer, condenser and dropping funnel were added 10 grams (0.064 mole) of $VCl_3$, 125 cc. of toluene, and 18.1 gm. (0.192 mole) of triethylamine. In the dropping funnel was placed 51.6 gm. (0.192 mole) of di-n-amylphosphorodithoic acid. The acid was added to the material in the flask over a 30 minute period while the reaction was maintained under nitrogen. After the addition had been completed, the reaction temperature had risen to 45° C. from 25° C. The reaction mixture was then heated to 80° C. and was maintained between 80°–90° C. for four hours. The mixture was then cooled and filtered to remove the triethylamine-hydrochloride formed during the reaction.

The filtrate resulting from the above reaction was then stripped of solvent at reduced pressure (about 10 mm. Hg) and at a temperature of 60°–70° C. The red viscous oil that remained was collected as the product (50.4 gm.). The filtered precipitate of triethylamine-hydrochloride was dissolved in water and titrated for ionic chloride. It was calculated that 90% of the theoretical amount of chlorine was obtained as ionic chloride indicating a 90% conversion to the desired product. Analysis of the product showed the following: vanadium—5.68 wt. %; phosphorus—10.22 wt. % (Calc. for V=5.94 wt. % and for P=10.82 wt. %).

EXAMPLE 4

$VCl_3$ (10 gm. or 0.064 mole) was suspended in 125 cc. of toluene at room temperature. The mixture was heated up to 70° C. and 51.6 gm. (0.19 mole) of O,O-diamylphosphorodithioate acid was added. During the addition, nitrogen gas was passed through the solution to remove the HCl by-product. After the 60 minute addition, the reaction was heated to 80° C. and was maintained at this temperature for four hours. During the reaction, nitrogen gas was passed through the solution just below its surface in an effort to remove by-product HCl. Titration of the water trap residue showed that only a small amount (approx. 7%) of the desired HCl had been given off. Therefore, 18.1 gm. of dimethylpyridine was added as an acid acceptor for the HCl, and heating was continued for an additional four hours. The reaction mixture was then allowed to cool and was filtered.

The precipitated dimethylpyridine—HCl was dissolved in one liter of water and was titrated with AgNO$_3$. Eighty-one percent of the theoretical amount of HCl was determined. The filtrate was distilled to dryness leaving a red viscous oil weighing 51 gm. (theoretical yield=54.9 gm.).

EXAMPLE 5

$VCl_3$ (7.85 gm.) and triethylamine (14.25 gm.) were dissolved in 300 cc. of toluene. To this mixture was added 32.1 gm. of di-n-propylphosphorodithioic acid dropwise over a period of forty five minutes. The reaction mixture was stirred at room temperature for one hour and was then heated to 80° C. The reaction mixture was heated at 80°–90° C. for six hours. At the end of this time, the reaction mixture was cooled to room temperature and was filtered. The filtrate was stripped to dryness on a water aspirator to yield 34.8 gm. of product (35.0 gm.=theoretical yield) having a vanadium analysis of 7.02 wt. % (7.52 wt. %=theoretical).

Ten grams of the precipitate removed during the filtration step was dissolved in one liter of water and required 12.8 cc. of 0.1N silver nitrate to react to the equilibrium point. This indicated that 87% of the theoretical amount of chloride contained in the HCl by-product was removed from the reaction medium.

EXAMPLE 6

$VCl_3$ (7.85 gm.) and 14.25 gm. of triethylamine acid acceptor were dissolved in 300 cc. of toluene. To this mixture was added 32.1 gm. of O,O-diisopropylphosphorodithioic acid dropwise over a thirty minute period. The temperature of the reaction medium rose from 30° C. to 55° C. The reaction mixture was then heated to 60°–80° C. for two additional hours. At the end of the heating period, the reaction mixture was filtered using a diatomaceous earth filter media (CELITE brand) under a nitrogen atmosphere. The filtrate was then distilled at reduced pressure using a water aspirator vacuum to yield 33.5 gm. of product (theoretical=34.5 gm.). Analysis showed a vanadium content of 7.03 wt. % (theoretical=7.52 wt. %).

The precipitate recovered by filtration was dissolved in 400 cc. of water and gave a positive test for chloride. The solution was titrated with silver nitrate after dilution to 1000 ml. A 10 cc. aliquot of this solution needed 11.47 cc. of 0.1N silver nitrate indicating presence of 81% of the theoretical amount of chloride from the by-product HCl removed by the acid acceptor.

The foregoing Examples illustrate certain embodiments of the present invention but should not be construed in a limiting sense. The scope of protection desired is set forth in the claims which follow.

What is claimed:

1. A process for the formation of vanadium dialkyl phosphorodithioate compounds by reaction of a dialkyl phosphorodithioic acid with a vanadium halide in the presence of a substance capable of removing by-product hydrogen halide from the reaction medium.

2. A process as claimed in claim 1 wherein the acid contains $C_1$–$C_{10}$ alkyl groups.

3. A process as claimed in claim 1 wherein the vanadium halide is a vanadium chloride.

4. A process as claimed in claim 3 wherein the halide is $VOCl_3$.

5. A process as claimed in claim 3 wherein the halide is $VCl_3$.

6. A process as claimed in claim 1 wherein the substance is an inert gas.

7. A process as claimed in claim 6 wherein the inert gas is nitrogen.

8. A process as claimed in claim 1 wherein the substance is a chemical acid acceptor.

9. A process as claimed in claim 8 wherein the acceptor is an amine acid acceptor.

10. A process as claimed in claim 1 wherein the vanadium halide is a vanadium chloride, and the acid contains $C_1$–$C_{10}$ alkyl groups.

11. A process as claimed in claim 10 wherein the substance capable of removing by-product is an inert gas.

12. A process as claimed in claim 11 wherein inert gas is nitrogen.

13. A process as claimed in claim 1 wherein acid and vanadium halide are reacted in approximate stoichiometric amounts with one another.

14. A process as claimed in claim 10 wherein the acid and vanadium halide are reacted in approximate stoichiometric amounts with one another.

15. A process as claimed in claim 14 wherein nitrogen gas is used to remove by-product from the reaction medium.

* * * * *